US011192883B2

(12) United States Patent
Glover et al.

(10) Patent No.: US 11,192,883 B2
(45) Date of Patent: Dec. 7, 2021

(54) FUNCTIONALIZED MATERIALS AND COMPOUNDS

(71) Applicant: University of South Alabama, Mobile, AL (US)

(72) Inventors: Thomas Grant Glover, Spanish Fort, AL (US); Kevin N. West, Mobile, AL (US)

(73) Assignee: University of South Alabama, Mobile, AL (US)

( * ) Notice: Subject to any disclaimer, the term of this patent is extended or adjusted under 35 U.S.C. 154(b) by 0 days.

(21) Appl. No.: 17/288,122

(22) PCT Filed: Oct. 25, 2019

(86) PCT No.: PCT/US2019/058022
§ 371 (c)(1),
(2) Date: Apr. 23, 2021

(87) PCT Pub. No.: WO2020/086938
PCT Pub. Date: Apr. 30, 2020

(65) Prior Publication Data
US 2021/0309643 A1  Oct. 7, 2021

Related U.S. Application Data

(60) Provisional application No. 62/751,082, filed on Oct. 26, 2018.

(51) Int. Cl.
C07D 403/12 (2006.01)
C07D 233/74 (2006.01)
D06M 13/165 (2006.01)
D06M 13/348 (2006.01)
D06M 101/06 (2006.01)

(52) U.S. Cl.
CPC ......... C07D 403/12 (2013.01); C07D 233/74 (2013.01); D06M 13/165 (2013.01); D06M 13/348 (2013.01); D06M 2101/06 (2013.01)

(58) Field of Classification Search
CPC .................................. D06M 13/348
See application file for complete search history.

(56) References Cited

U.S. PATENT DOCUMENTS

| 4,021,424 | A | 5/1977 | Grabinger et al. |
| 4,035,146 | A | 7/1977 | Brenner et al. |
| 5,614,625 | A | 3/1997 | Broadhurst et al. |
| 6,120,562 | A | 9/2000 | Patsch et al. |
| 8,927,682 | B2 | 1/2015 | Baker et al. |
| 8,956,839 | B2 | 2/2015 | Rambo et al. |
| 8,962,823 | B2 | 2/2015 | Cordova et al. |
| 9,394,377 | B2 | 7/2016 | Son et al. |
| 9,962,691 | B2 | 5/2018 | Ragheb et al. |
| 2015/0233049 | A1 | 8/2015 | Delattre |
| 2017/0218099 | A1 | 8/2017 | Dire et al. |

FOREIGN PATENT DOCUMENTS

| CN | 105474015 A | * | 4/2016 | .......... C07D 495/04 |
| CN | 106637960 A | * | 5/2017 | |

OTHER PUBLICATIONS

Lataca "The Synthesis of 1,3,5-triazine Derivatives and JNJ7777120 Analogues with Histamine H4 Receptor Affinity and Their Interaction with PTEN Promoter", Chem. Biol. Drug Des. 2016, 88, 254-263 (Year: 2016).*
Pubchem. CID 597696, Mar. 27, 2005, pp. 1-8; retrieved from Internet https://pubchem.ncbi.nlm.nih.gov/compound/597696 ; p. 2, formula.
Whittaker et al., "Deisgn and Therapeutic Application of Matrix Metaloproteinase Inhibitors"; Sep. 8, 2009, Chemical Reviews: vol. 99, Issue 9, pp. 2735-2776; p. 2749, compound 98.
Pubchem. CID 20623906. Dec. 5, 20017, pp. 1-9; retrieved from Internet https://pubchem.ncbi.nlm.nih.gov/compound/20623906 p. 2, formula.

* cited by examiner

Primary Examiner — Nicole M. Buie-Hatcher
(74) Attorney, Agent, or Firm — Foryt Patent Services LLC

(57) ABSTRACT

Processes for chemical functionalization of materials is described. The processed generally include chemical reaction between a thiol group of a first compound or material and an alkane group or alkyne group of a second compound or material. Also disclosed are functionalized materials and compounds suitable for functionalizing a material.

19 Claims, No Drawings

FUNCTIONALIZED MATERIALS AND COMPOUNDS

FIELD OF THE INVENTION

The present invention relates generally to processes for imparting one or more desirable functionalities to materials and compounds which prior to treatment according to the process essentially lack such functionality.

BACKGROUND OF THE INVENTION

It is known in the art to impart desirable characteristics or performance attributes to materials by applying chemical compounds thereto. For example, materials may be coated or treated with various chemical compositions that contain one or more ingredients that impart hydrophobicity, soil or stain resistance, antistat, UV antidegradant, antibacterial/biocidal or similar characteristics which are sought after in various product and end-use applications. A particular challenge for manufacturers in developing coatings or treatment compositions in this field resides in (i) identifying active ingredients that are rapidly and thoroughly soluble or dispersible in composition solvents or carriers, in particular in solvents that are often utilized today because of their environmentally friendly nature while (ii) maximizing the coating's or treatment's efficacy and efficacy duration. Despite best efforts, the nature of these coatings or treatments is that their efficacy will inevitably decrease over time.

In order to improve efficacy duration, the art has investigated techniques that involve the chemical bonding or linking of a functional compound to the molecular structure of a material. In the field of antimicrobials, for example, the chemical bonding of antimicrobial compounds to natural and man-made substrates and materials to impart antimicrobial efficacy thereto has previously been explored as a desirable alternative to applying antimicrobial compound-containing coatings and adhesives thereto. For example, U.S. Patent Application Publication No. 2015/0233049 discloses a wash-durable textile article comprising a textile substrate, an antimicrobial metal nanoparticle, and a linking agent chemically bonding the antimicrobial metal nanoparticle to the substrate. U.S. Pat. No. 9,394,377 discloses a method for producing an antimicrobial fiber by reacting a reactive compound with an antimicrobial agent to prepare a reactive antimicrobial compound, chemically fixing the reactive antimicrobial compound to a cellulose fiber through chemical bonding between the reactive compound and the cellulose and stabilizing the cellulose fiber structure. Less recently, U.S. Pat. No. 4,035,146 disclosed a method for bonding certain named antimicrobials to a cellulose, starch or leather substrate that includes reacting the substrate with cyanuric chloride in a solution to chemically bond it to the substrate and then reacting the antimicrobial in solution with the cyanuric chloride to chemically bond the cyanuric chloride to the antimicrobial.

Recent advances in reaction chemistry have given rise to a class of reactions labeled "click chemistry" as described for example in U.S. Pat. No. 8,927,682. One subset of this class, known in the art as "thiol-ene" click chemistry reactions as their mechanism involves the reaction between a thiol group of a first compound and an alkene group of a second compound, have been described as purportedly useful in both polymerization and functionalization. U.S. Pat. Nos. 9,962,691, 8,956,839 and 8,962,823, the contents and description of each of which are hereby expressly incorporated herein by reference, are examples providing background in this regard.

The general desirability of such processes and products, and their preference in the marketplace, resides in the general notion that the efficacy is purportedly retained longer through chemical bonding than through nonreactive coating or adhesive application. This is especially applicable in harsh substrate end-use applications that include for example prolonged exposure to sunlight, severe weather, abrasive conditions and/or aggressive repetitive washing with cleaners and detergents. Nonetheless, prior art chemical bonding processes have shown various drawbacks in development. For example, prior processes for linking antimicrobial compounds to substrates can be complex, involving multiple reaction steps and linking groups and requiring carefully monitored and controlled reaction conditions— which translate to significant cost and efficiency challenges, particularly in scale-up to commercial production levels. In particular with respect to processing, prior methods often require the use of harsh solvents (see e.g. the use of dioxane or acetone in above-referenced U.S. Pat. No. 4,035,146), thereby introducing another challenge in handling, waste disposal and environmental regulatory compliance. Also, only a limited class of functional compounds possess chemical structures capable of bonding to materials or substrates (either directly or through linking groups), and even fewer demonstrate that capability while maintaining the efficacy they exhibit in their unbonded form. Finally, though chemical bonded functionalities generally exhibit improved performance over functionalities imparted via coatings and adhesives, many do not exhibit the efficacy (for example antimicrobial functionality as quantified by log kill rate) and/or efficacy duration required for many demanding applications in today's marketplace.

A continuing need therefore exists for chemical compounds that exhibit at least one desirable functionality and whose successful use in functionalizing materials or substrates may be achieved using lower-cost, environmentally preferable and generally mild materials and reaction conditions.

SUMMARY OF THE INVENTION

In one aspect, the present invention relates to a process for chemical functionalization wherein the process includes reacting an unsaturated compound selected from the group consisting of an alkene compound of the formula

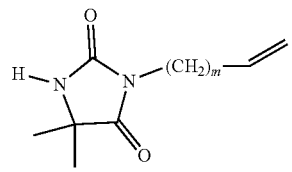

and an alkyne compound of the formula

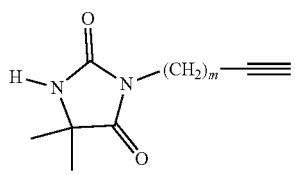

wherein m is an integer between 1 and 22 inclusive; with a thiol reactant at the thiol moiety thereof, said thiol reactant selected from the group consisting of a thiol-containing compound and a material that comprises a pendant thiol moiety.

In another aspect, the present invention relates to process for chemical functionalization wherein the process includes reacting a thiol compound of the formula

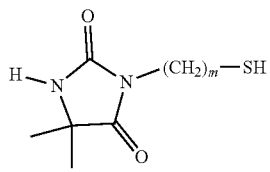

wherein m is an integer between 1 and 22 inclusive with an unsaturated reactant selected from the group consisting of an alkene reactant and an alkyne reactant, wherein said alkene reactant is selected from the group consisting of (i) an alkene-containing compound and (ii) a material that comprises a pendant alkene moiety and wherein said alkyne reactant is selected from the group consisting of (i) an alkyne-containing compound and (ii) a material that comprises a pendant alkyne moiety.

In yet another aspect, the present invention relates to a functionalized material of the formula

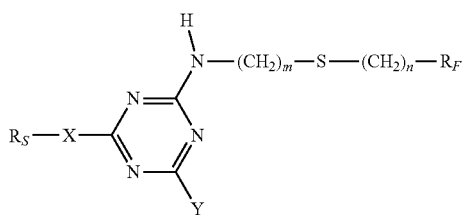

wherein $R_S$ is a material that, prior to functionalization, includes a pendant amino, amido, imino or hydroxyl group; X is selected from the group consisting of O and N; Y is selected from the group consisting of Cl, OH and $NH_2$; m is an Integer between 1 and 22 inclusive; n is an integer between 1 and 22 inclusive; and $R_F$ is a functionality imparting group.

In still another aspect, the present invention relates to a compound suitable for example for functionalizing a material wherein the compound has the formula:

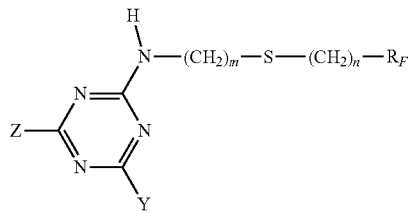

wherein Y and Z are each independently selected from the group consisting of Cl, OH and $NH_2$; m is an integer between 1 and 22 inclusive; n is an integer between 1 and 22 inclusive; and $R_F$ is a functionality imparting group.

Further aspects of the present invention and areas of applicability will become apparent from the description provided herein. It should be understood that the description and specific examples are intended for purposes of illustration only and are not intended to limit the spirit and scope of the present invention.

DETAILED DESCRIPTION

As utilized herein, the following terms or phrases are defined as follows:

"Alkene" means a chemical structure or substructure that contains a non-aromatic carbon-carbon double bond.

"Alkyne" means a chemical structure or substructure that contains a carbon-carbon triple bond.

"Thiol" means a chemical structure or substructure that contains a sulfur with an H—S bond.

"cyanuric chloride" means a compound with a nitrogen containing ring and three formula

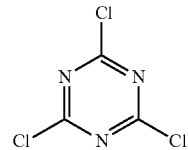

as well as, where applicable, cyanuric chloride derivatives or cyanuric chloride-based structures, including those that are formed as compounds or chemical intermediates when performing processes or methods of the present invention.

In a general sense, the present invention employs "thiol-ene" click chemistry to impart certain functionality to materials. Thiol-ene click chemistry in general is a phrase used to describe reactions wherein a thiol group of a thiol group-containing compound or material reacts with an alkene or alkyne group of an alkene- or alkyne-containing compound or material. The present invention therefore is broadly directed to processes for functionalization of materials that include chemical reaction between a thiol group of a first compound or material and an alkene group or alkyne group of a second compound or material.

In a first aspect, then, the present invention is directed to a process for chemical functionalization wherein the process includes reacting an unsaturated compound selected from a group consisting of an alkene compound of the formula

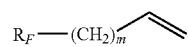

and an alkyne compound of the formula

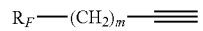

wherein for each unsaturated compound m is an integer between 1 and 22 inclusive and $R_F$ is a functionality imparting group;
with a thiol reactant. The thiol reactant may be selected from the group consisting of a thiol-containing compound or a material that comprises a pendant thiol moiety.

The group $R_F$, referred to herein as a "functionality imparting group", is contemplated to be a chemical group or moiety that is capable of imparting functionality to a compound and/or a functionalized material which includes it. Non-limiting examples include groups that may impart one or more of polarity, hydrophobicity, hydrophilicity, oleophilicity, oleophobicity, ominphilicity, omniphobicity, Lewis acidity, Lewis basicity, Bronsted acidity, Bronsted basicity, nucleophilicity, electrophilicity, antimicrobial, biocidal or fungicidal activity and the like, as well as groups capable of exhibiting such functionality upon activation, reactivation or other chemical treatment.

An important advantage of the present invention lies in the fact that the reacting step is effectively initiated by the presence of low-cost and environmentally friendly initiators such as hydrogen peroxide. Accordingly, in one or more embodiments, the reacting step is performed in the presence of hydrogen peroxide.

In one or more embodiments, the unsaturated compound is selected from the group consisting of an alkene compound of the formula

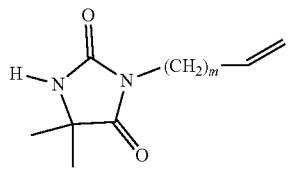

and an alkyne compound of the formula

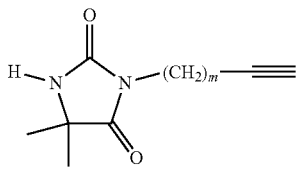

wherein for each unsaturated compound m is an integer between 1 and 22 inclusive.

Accordingly, in one or more embodiments, the process of the present invention is a process for chemical functionalization, said process comprising reacting an unsaturated compound selected from the group consisting of an alkene compound of the formula

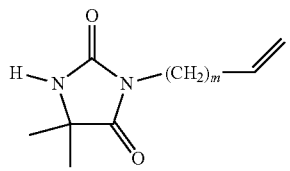

and an alkyne compound of the formula

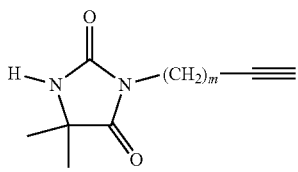

wherein for each unsaturated compound m is an integer between 1 and 22 inclusive;
with a thiol reactant, said thiol reactant selected from the group consisting of a thiol-containing compound and a material that includes a pendant thiol moiety. In one or more embodiments, the unsaturated compound is an alkene compound having the formula

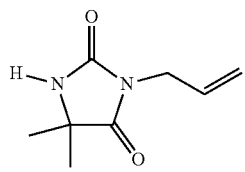

In one or more embodiments, the thiol reactant is a material that includes a pendant thiol moiety and the process of the present invention may be described as a process for functionalizing a material. Materials that include a pendant thiol moiety may include for example silk, wool and human hair. In one or more embodiments, the process of the present invention includes a step of forming a material that includes a pendant thiol moiety. The forming step may include chemically modifying a material essentially devoid of pendant thiol moieties to include a pendant thiol moiety. In one or more embodiments, the chemically modifying step includes reacting a material comprising pendant amino, amido, imino or hydroxyl groups with cyanuric chloride or a derivative thereof.

Suitable materials that include pendant amino, amido, imino or hydroxyl groups include by way of non-limiting example cellulose; vegetable fibers such as cotton, hemp, jute, flax, ramie, sisal, bagasse, pina, esparto, Indian hemp, hoopvine, kenaf, linden bast, nettle bast, papyrus, Manila hemp, sisal, bowstring hemp, henequen, phormium, yucca, coir, kapok, milkweed, luffa, and bamboo fiber; wool or other animal fibers such as silkworm silk, spider silk, sinew, catgut, wool, sea silk, hair, cashmere wool, mohair, nutria or coypu pelt, angora, sheep pelt, rabbit pelt, mink pelt, fox pelt, beaver pelt, angora, bison, qiviut, horsehair, chiengora, alpaca wool, vicuna wool, merino wool, yak down, camel down, guanaco wool, llama wool, and chinchilla; wood, wood fibers and wood products such as groundwood thermos-mechanical pulp, bleached or unbleached kraft or sulfite pulps, engineered wood products, engineered paper products, tissue, paper, paper and polymer composites, gauze pads, fiberboard, paper, wood boards, wood chips and mulch; plants, plant components and plant by-products seeds and seed pods; aerosolized dust or spray; glass products such as fiberglass and glass wool; and synthetic or man-made materials such as polymers, thermoplastics, thermosets and the like including nylon, modacrylic, olefin, acrylic, polyester, carbon fiber, reinforced plastics, rayon, diacetate, triacetate, polyester-polyurethane copolymers and synthetic clays. Unfunctionalized materials may come in various forms, for example fibers, fabrics, pellets, powders, films or solid surfaces. It should be understood that unfunctionalized materials include materials that exhibit certain functionalities or efficacies achieved through other aspects of their molecular structure are nonetheless considered unfunctionalized materials hereunder when failing within the scope of definition set forth above.

A suitable material that includes a pendant thiol moiety is a material of the formula

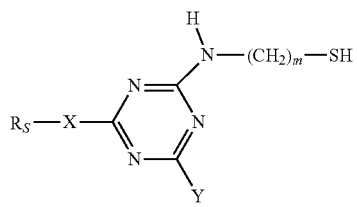

wherein $R_S$ is a material that, prior to functionalization, includes a pendant amino, amido, imino or hydroxyl group; X is selected from the group consisting of O and N; Y is selected from the group consisting of Cl, OH and $NH_2$; and m is an integer between 1 and 22 inclusive.

In one or more embodiments, the thiol reactant is a thiol-containing compound. In one or more embodiments, thiol-containing compounds include, in addition to at least one thiol moiety, one or more moieties capable of covalently bonding with materials that include pendant amino, amido, imino or hydroxyl groups. Such moieties include, by way of non-limiting example, Cl, OH, $NH_2$ and cyanuric chloride and derivatives thereof.

In one or more embodiments, the process of the present invention may include forming the thiol-containing compound. The step of forming the thiol-containing compound may include reacting a compound of the formula

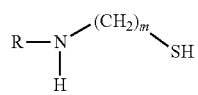

wherein R is selected from the group consisting of H, alkyl, alkenyl and aromatic groups and m is an integer between 1 and 22 inclusive with cyanuric chloride or a derivative thereof. In one or more embodiments, the compound of the formula

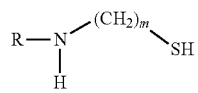

wherein R is selected from the group consisting of H, alkyl, alkenyl and aromatic groups and m is an integer between 1 and 22 inclusive is cysteamine and the step of forming the thiol-containing compound includes reacting cysteamine with cyanuric chloride or a derivative thereof.

In one or more embodiments, the step of forming the thiol-containing compound may include reacting cysteine with cyanuric chloride or a derivative thereof.

In one or more embodiments, the process of the present invention may further include covalently bonding the reaction product of the thiol-containing compound and the unsaturated compound in the reacting step to a material comprising pendant amino, amido, imino or hydroxyl groups.

In another aspect, the process of the present invention is directed to a process for chemical functionalization wherein the process includes reacting a thiol compound of the formula

wherein m is an integer between 1 and 22 inclusive and $R_F$ is a functionality imparting group as elsewhere herein defined.

with an unsaturated reactant selected from the group consisting of an alkene reactant and an alkyne reactant. The alkene reactant may be selected from the group consisting of (i) an alkene-containing compound and (ii) a material that comprises a pendant alkene moiety. The alkyne reactant may be selected from the group consisting of (i) an alkyne-containing compound and (ii) a material that comprises a pendant alkyne moiety.

An important advantage of the present invention lies in the fact that the reacting step is well initiated by the presence of low-cost and environmentally friendly initiators such as hydrogen peroxide. Accordingly, in one or more embodiments, the reacting step is performed in the presence of hydrogen peroxide.

In one or more embodiments, the thiol compound has the formula

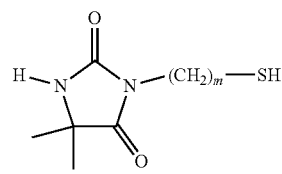

wherein m is an integer between 1 and 22 inclusive

Accordingly, in one or more embodiments, the process of the present invention is a process for chemical functionalization wherein process comprising reacting a thiol compound of the formula

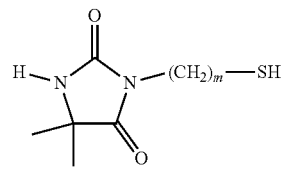

wherein m is an integer between 1 and 22 inclusive; with an unsaturated reactant selected from the group consisting of an alkene reactant and an alkyne reactant. The alkene reactant may be selected from the group consisting of (i) an alkene-containing compound and (ii) a material that comprises a pendant alkene moiety. The alkyne reactant may be selected from the group consisting of (i) an alkyne-containing compound and (ii) a material that comprises a pendant alkyne moiety. In one or more embodiments, the thiol compound has the formula

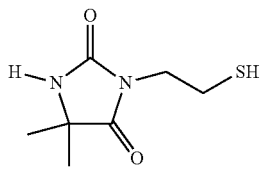

In one or more embodiments, the unsaturated reactant is a material that includes either a pendant alkene or a pendant alkyne moiety and the process of the present invention may be described as a process for functionalizing a material. Materials that include a pendant alkene or a pendant alkyne moiety as used herein are defined to include without limitation polymers that have alkene or alkyne groups that are part of or pendant from their polymer chain, for example butadiene polymers and copolymers such as ABS.

In one or more embodiments, the process of the present invention includes a step of forming a material that includes a pendant alkene moiety. The forming step may include chemically modifying a material essentially devoid of pendant alkene moieties to include a pendant alkene moiety. In one or more embodiments, the chemically modifying step includes reacting a material comprising pendant amino, amido, imino or hydroxyl groups with cyanuric chloride or a derivative thereof. Suitable materials that include pendant amino, amido, imino or hydroxyl groups include by way of non-limiting example those listed elsewhere herein.

In one or more embodiments, the process of the present invention includes a step of forming a material that includes a pendant alkyne moiety. The forming step may include chemically modifying a material essentially devoid of pendant alkyne moieties to include a pendant alkyne moiety. In one or more embodiments, the chemically modifying step includes reacting a material comprising pendant amino, amido, imino or hydroxyl groups with cyanuric chloride or a derivative thereof. Suitable materials that include pendant amino, amido, imino or hydroxyl groups include by way of non-limiting example those listed elsewhere herein.

A suitable material with a pendant alkene moiety includes a material of the formula

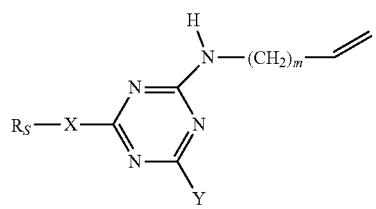

wherein $R_S$ is a material that, prior to functionalization, includes a pendant amino, amido, imino or hydroxyl group; X is selected from the group consisting of O and N; Y is selected from the group consisting of Cl, OH, $NH_2$; and m is an integer between 1 and 22 inclusive.

A suitable material with a pendant alkyne moiety includes a material with the formula

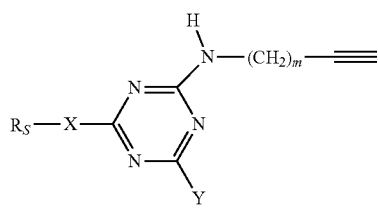

wherein $R_S$ is a material that, prior to functionalization, includes a pendant amino, amido, Imino or hydroxyl group; X is selected from the group consisting of O and N; Y is selected from the group consisting of Cl, OH, $NH_2$; and m is an integer between 1 and 22 inclusive.

In one or more embodiments, the alkene reactant is an alkene-containing compound while, in one or more embodiments, the alkyne reactant is an alkyne-containing compound. In one or more embodiments, alkene-containing compounds include, in addition to at least one alkene moiety, one or more moieties capable of covalently bonding with materials that include pendant amino, amido, imino or hydroxyl groups. Such moieties include, by way of non-limiting example, Cl, OH, $NH_2$ and cyanuric chloride and derivatives thereof. In one or more embodiments, alkyne-containing compounds include, in addition to at least one alkyne moiety, one or more moieties capable of covalently bonding with materials that include pendant amino, amido, imino or hydroxyl groups. Such moieties include, by way of non-limiting example, Cl, OH, $NH_2$ and cyanuric chloride and derivatives thereof.

In one or more embodiments, the process of the present invention may include forming the alkene-containing compound. The forming step may include reacting an aminoalkene compound of the formula

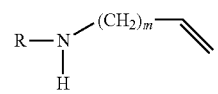

wherein R is selected from the group consisting of H, aryl, alkenyl and aromatic groups and m is an integer between 1 and 22 inclusive;
with cyanuric chloride or a derivative thereof.

In one or more embodiments, the process of the present invention may include forming the alkyne-containing compound. The forming step may include reacting of the formula

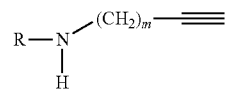

wherein R is selected from the group consisting of H, aryl, alkenyl and aromatic groups and m is an integer between 1 and 22 inclusive;
with cyanuric chloride or a derivative thereof.

In one or more embodiments, the aminoalkene compound is allylamine.

In one or more embodiments, the process of the present invention may include covalently bonding the reaction product of the alkene-containing compound and the thiol compound from the reacting step to a material that includes pendant amino, amido, imino or hydroxyl groups to form a functionalized material. In one or more embodiments, the process of the present invention may include covalently bonding the reaction product of the alkyne-containing compound and the thiol compound in the reacting step to a material that includes pendant amino, amido, imino or hydroxyl groups to form a functionalized material.

In one or more embodiments, the process of the present invention further includes treating the reaction product of the unsaturated compound and the thiol reactant in the reacting step a with halogen-containing material such as chlorine-containing and bromine-containing materials. Suitable materials for such treatment step include chlorine bleach, liquid chlorine, sodium hypochlorite, sodium hydrobromite, aqueous bromine and the like. In one or more embodiments, the treatment step may be periodically repeated. In one or more embodiments, the process of the present invention further includes treating the reaction product of the thiol compound and the unsaturated reactant in the reacting step a with halogen-containing material such as chlorine-containing materials and bromine-containing materials. Suitable materials for such treatment step include chlorine bleach, liquid chlorine, sodium hypochlorite, sodium hydrobromite, aqueous bromine and the like. In one or more embodiments, the treatment step may be periodically repeated.

In another aspect, the present invention is directed to a functionalized material. The functionalized material of the present invention is a functionalized material of the formula:

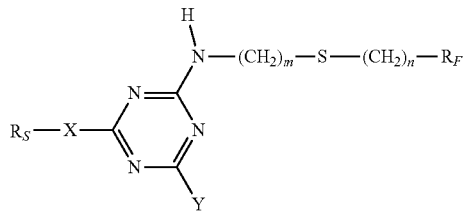

wherein $R_S$ is a material that, prior to functionalization, includes a pendant amino, amido, imino or hydroxyl group; X is selected from the group consisting of O and N; Y is selected from the group consisting of Cl, OH and $NH_2$; m is an integer between 1 and 22 inclusive; n is an integer between 1 and 22 inclusive; and $R_F$ is a functionality imparting group.

In one or more embodiments, the functionalized material of the present invention has the formula

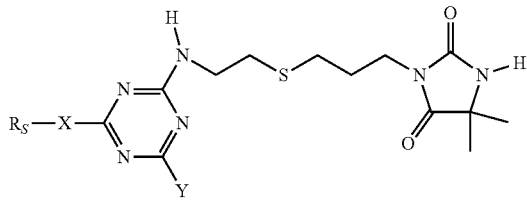

wherein $R_S$ is a material that, prior to functionalization, includes a pendant amino, amido, imino or hydroxyl group; X is selected from the group consisting of O and N and Y is selected from the group consisting of Cl, OH and $NH_2$.

Such functionalized materials can exhibit antimicrobial and antifungal efficacy upon activation with, for example, halogen-containing materials such as chlorine-containing and bromine-containing materials. Suitable materials for such activation include chlorine bleach, liquid chlorine, sodium hypochlorite, sodium hydrobromite, aqueous bromine and the like. Further, such efficacy can be reactivated over time as/if needed with subsequent similar treatments with these compounds.

In another aspect, the present invention is directed to a compound that is for example suitable for functionalizing a material comprising pendant amino, amido, imino or hydroxyl groups by covalently bonding thereto. The compounds of the present invention have the general formula:

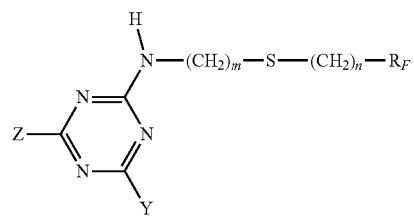

wherein Y and Z are each independently selected from the group consisting of Cl, OH and $NH_2$; m is an integer between 1 and 22 inclusive; n is an integer between 1 and 22 inclusive; and RE is a functionality imparting group.

In one or more embodiments, the compound of the present invention has the formula

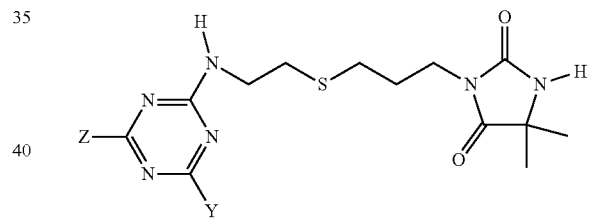

wherein Y and Z are each independently selected from the group consisting of Cl, OH and $NH_2$.

The following example, while provided to illustrate with specificity and detail the many aspects and advantages of the present invention, is not be interpreted as in any way limiting its scope. Variations, modifications and adaptations which do depart of the spirit of the present invention will be readily appreciated by one of ordinary skill in the art.

Formation of alkene compound. 2.0 g of NaOH was dissolved in 25 mL of water in a 250 ml Erlenmeyer flask. 6.4 g of 5,5-Dimethylhydantoin (DMH) was the added to the solution which was then stirred/swirled to allow the DMH to be deprotonated as it dissolves, driving its complete dissolution. 10 mL of MeOH was then added to the solution flask (to increase the solubility of the allyl bromide.) The solution was then heat slowly to 60° C. (covering with parafilm) and 4.4 ml of allyl bromide was added slowly over an hour to allow for reaction of the allyl bromide with the deprotonated hydantoin, but to minimize the polymerization of the allyl bromide. The allyl bromide was added in increments small enough to maintain a homogeneous (clear) solution, or to minimize cloudiness (2 phases). The product mixture was then allowed to cool to room temperature.

The alkene compound Allyl 5,5-Dimethylhydantoin (ADMH) was precipitated from the product solution by immersing it in an ice bath and adding 1.0 g of NaCl. The solid precipitate was then filtered under vacuum and allowed to dry. Yields for runs performed were each greater than 90%.

Formation of material with pendant thiol moiety. The preparation was for 9 0.5"×0.5" swatches of T-shirt weave white cotton fabric material, which were prewashed with soap and water, then acetone or chloroform and allowed to dry in air.

50 mL of water was placed in a 100 mL beaker. 5 g of sodium carbonate was added, and the solution was heated to 65° C. The swatches were added to the beaker and stirred for 5-10 minutes. 40 ml of chloroform was added to a 100 mL Erlenmeyer flask. 1.88 g of cyanuric chloride was added this flask and the solution was stirred to dissolve the solid. The swatches were then removed from the aqueous solution and immersed in the chloroform solution, stirring for 1 hour, with the flask capped with a vented stopper. After one hour, the swatches were transferred to a beaker containing 20 mL of water and 0.5 g of cysteamine. The fabric swatches were allowed to stir for 22-24 hours in this solution, after which they were washed with water and chloroform or acetone and allowed to dry in air.

Reaction of alkene compound with material (cotton) containing pendant thiol moiety. 2-3 ml of tetrahydrofuran (THF) was saturated with azobisisobutyronitrile (AIBN) and then coated over the fabric swatches, which were then allowed to dry in air for 5 minutes. Approximately 10 g of ADMH as formed above was heated to melting (~70° C.) and held at constant temperature. The swatches were placed in the molten ADMH at temperature for 1 hour. Afterward the swatches were removed and rinsed with acetone and water, then dried in air.

ATR-IR spectra of the DMH, ADMH, untreated cotton and functionalized cotton material were collected to confirm reaction product formation for the above steps.

Efficacy Testing of Functionalized Fabric. The bacteria *Serratia marcesens* was selected to test for efficacy against bacterial growth as it produces a visibly discernable dark pink color as a function of its growth in nutrient supportive broth once incubated at 30° C. It should also be incidentally noted that *S. marcesens* may produce a virtually imperceptible (to the human eye) amount of light pink color when incubated at temperatures higher than 30° C. such as 37° C. Result interpretation is based on visual observation where either *S. marcesens* growth or no growth is visibly detected based on color generation, with development of a dark pink color after 24 hours' incubation at 30° C. under ambient conditions clearly shows *S. marcesens* growth on light colored fabric samples. Fabric treated with a suspected biocide agent that lacks similar color development indicates that *S. marcesens* growth is inhibited and displays biocidal action.

Six 12 mm×12 mm functionalized cotton fabric squares were cur from the functionalized cotton material formed above. Each of these six samples were placed in a separate well of a 12-well clear plastic microplate. Six 12 mm×12 mm control samples of standard unfunctionalized cotton fabric were placed (one each) in the remaining six wells of the 12-well microplate. Three of these six functionalized cotton samples and three of the control samples were further treated by applying commercially available Clorox™ bleach.

The incubation procedure involved preparing a *S. marcesen* bacterial suspension in Muller-Hinton broth (M-H) matching a 0.5% McFarland turbidity standard. This yielded approximately $1\times10^8$ bacteria/milliliter (mL). A 1:100 dilution of the suspension is made to reduce bacterial numbers. A 50 microliter (µL) drop of the 1:100 dilution of bacterial suspension was added to center of each fabric sample. Microplates are incubated at 30° C. under ambient air conditions for 24 hours (+/−30 minutes) without $CO_2$. After incubation, microplates are removed from the incubator. Fabric samples were visibly inspected by persons with no knowledge of the sample identity and examined for the presence or absence of color with results are logged as either ++ for a dark pink color (indicating no appreciable antibacterial activity (A1-A3 and D1-D3); + for a less dark pink color (indicating limited antibacterial activity (C1-C3); +/− for a slightly pink color (indicating medium antibacterial activity (B1-B3); and − for essentially white or unchanged color (indicating high antibacterial activity [[against the number of bacteria ($4.0\times10^5$ bacteria/mL) placed on each fabric sample]]. The results are listed in Table 1 below.

TABLE 1

| Sample Number | Description | Color Assessment |
|---|---|---|
| A1 | control, no bleach | ++ |
| A2 | control, no bleach | ++ |
| A3 | control, no bleach | ++ |
| B1 | functionalized, with bleach | − |
| B2 | functionalized, with bleach | +/− |
| B3 | functionalized, with bleach | +/− |
| C1 | functionalized, no bleach | + |
| C2 | functionalized, no bleach | + |
| C3 | functionalized, no bleach | + |
| D1 | control with bleach | + |
| D2 | control with bleach | + |
| D3 | control with bleach | ++ |

As evidenced by the results of the above testing, the chemical functionalization process of the present invention generates a functionalized material that when treated with a with halogen-containing material such as chlorine bleach demonstrates antimicrobial/antibacterial efficacy.

The invention claimed is:

1. A process for chemical functionalization wherein the process includes reacting an alkene compound of the formula

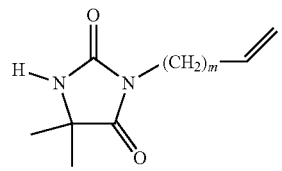

wherein m is an integer between 1 and 22 inclusive with a thiol reactant at the thiol moiety thereof, said thiol reactant selected from the group consisting of a thiol-containing compound and a material that comprises a pendant thiol moiety.

2. The process of claim 1 wherein said alkene compound has the formula:

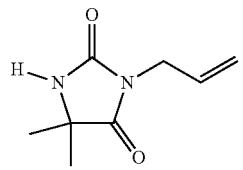

3. The process of claim 1 wherein said thiol reactant is a material that comprises a pendant thiol moiety.

4. The process of claim 1 further comprising forming said material that comprises a pendant thiol moiety, said forming step comprising chemically modifying a material essentially devoid of pendant thiol moieties to include a pendant thiol moiety.

5. The process of claim 4 wherein said chemically modifying step comprises reacting a material comprising pendant amino, amido, imino or hydroxyl groups with cyanuric chloride or a derivative thereof.

6. The process of claim 1 wherein thiol reactant is a thiol-containing compound.

7. The process of claim 6 further comprising the step of forming said thiol-containing compound, said forming step comprising reacting a compound of the formula

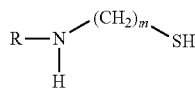

wherein R is selected from the group consisting of H, alkyl, alkenyl and aromatic groups and m is an integer between 1 and 22 inclusive with cyanuric chloride or a derivative thereof to form said thiol-containing compound.

8. The process of claim 7 wherein said compound of the formula

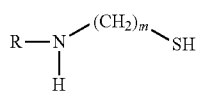

wherein R is selected from the group consisting of H, alkyl, alkenyl and aromatic groups and m is an integer between 1 and 22 inclusive is cysteamine.

9. The process of claim 6 further comprising the step of covalently bonding the reaction product of said thiol-containing compound and said alkene from said reacting step to a material comprising pendant amino, amido, imino or hydroxyl groups.

10. The process of claim 6 further comprising the step of forming said thiol-containing compound, said forming step comprising reacting cysteine with cyanuric chloride or a derivative thereof.

11. A process for chemical functionalization, said process comprising reacting a thiol compound of the formula:

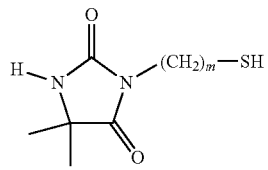

wherein m is an integer between 1 and 22 inclusive;

with an alkene reactant at the alkene moiety thereof, said alkene reactant selected from the group consisting of an alkene-containing compound or a material that comprises a pendant alkene moiety.

12. The process of claim 11 wherein said thiol compound has the formula

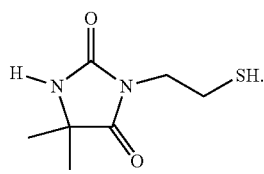

13. The process of claim 11 wherein said alkene reactant is a material that comprises a pendant alkene moiety.

14. The process of claim 13 further comprising a step of forming said material that comprises a pendant alkene moiety, said forming step comprising chemically modifying a material essentially devoid of pendant alkene moieties to include a pendant alkene moiety.

15. The process of claim 14 wherein said chemically modifying step comprises reacting a material comprising pendant amino, amido, imino or hydroxyl groups with cyanuric chloride or a derivative thereof.

16. The process of claim 11 wherein said alkene reactant is an alkene-containing compound.

17. The process of claim 16 further including the step of forming said alkene-containing compound, said forming step comprising reacting a compound of the formula

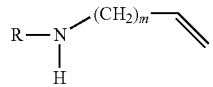

wherein R is selected from the group consisting of H, aryl, alkenyl and aromatic groups and m is an integer between 1 and 22 inclusive with cyanuric chloride or a derivative thereof to form said alkene-containing compound.

18. The process of claim 16 further comprising the step of covalently bonding the reaction product of said alkene-containing compound and said thiol compound from said reacting step to a material comprising pendant amino, amido, imino or hydroxyl groups.

19. A compound suitable for functionalizing a material comprising pendant amino, amido, imino or hydroxyl groups, said compound having the formula:
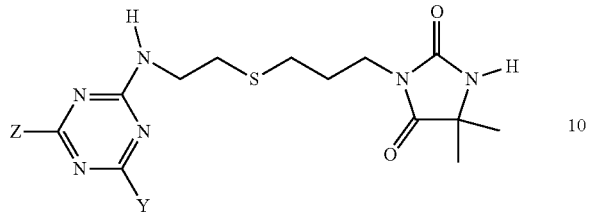
Wherein Y and Z are each independently selected from the group consisting of Cl, OH and $NH_2$.
* * * * *

UNITED STATES PATENT AND TRADEMARK OFFICE
CERTIFICATE OF CORRECTION

| | | |
|---|---|---|
| PATENT NO. | : 11,192,883 B2 | Page 1 of 1 |
| APPLICATION NO. | : 17/288122 | |
| DATED | : December 7, 2021 | |
| INVENTOR(S) | : Glover et al. | |

It is certified that error appears in the above-identified patent and that said Letters Patent is hereby corrected as shown below:

In the Specification

In Column 1, after the title and directly above "FIELD OF THE INVENTION," insert:
--STATEMENT REGARDING FEDERALLY SPONSORED RESEARCH OR DEVELOPMENT
This invention was made with government support under grant number W911NF-16-2-0099 awarded by the ARMY/ARO. The government has certain rights in the invention.--

Signed and Sealed this
Third Day of January, 2023

Katherine Kelly Vidal
*Director of the United States Patent and Trademark Office*